(12) United States Patent
Mane et al.

(10) Patent No.: US 7,737,107 B2
(45) Date of Patent: Jun. 15, 2010

(54) TRIMETHYLCYCLODODECATRIENE DERIVATIVES, USE THEREOF AND PERFUMED PRODUCTS CONTAINING THE SAME

(75) Inventors: Jean Mane, Grasse (FR); Jean-Jacques Chanot, Speracedes (FR); Martin Schroeder, Ashford (GB)

(73) Assignee: V. Mane Fils, Bar-sur-Loup (FR)

( * ) Notice: Subject to any disclaimer, the term of this patent is extended or adjusted under 35 U.S.C. 154(b) by 96 days.

(21) Appl. No.: 11/795,382

(22) PCT Filed: Jan. 13, 2006

(86) PCT No.: PCT/FR2006/000081

§ 371 (c)(1), (2), (4) Date: Sep. 17, 2007

(87) PCT Pub. No.: WO2006/077306

PCT Pub. Date: Jul. 27, 2006

(65) Prior Publication Data

US 2008/0139446 A1 Jun. 12, 2008

(30) Foreign Application Priority Data

Jan. 19, 2005 (FR) .................................. 05 00550

(51) Int. Cl.
- *A61K 8/00* (2006.01)
- *A61K 8/18* (2006.01)
- *C07C 41/00* (2006.01)
- *C07C 27/10* (2006.01)
- *C07C 29/10* (2006.01)
- *C07C 35/00* (2006.01)

(52) U.S. Cl. ............................ 512/1; 512/25; 568/579; 568/700

(58) Field of Classification Search .................. 512/25, 512/1; 568/579, 700
See application file for complete search history.

(56) References Cited

U.S. PATENT DOCUMENTS 3,723,478 A 3/1973 Ohloff et al.
3,845,078 A * 10/1974 Lemberg ..................... 549/513
4,460,498 A * 7/1984 Giersch et al. ................. 512/8

FOREIGN PATENT DOCUMENTS

FR 1528158 6/1968

OTHER PUBLICATIONS

Industrial & Engineering Chemistry Product Research and Development 1979 18 (4) pp. 254-258 Morikawa et al. In: Symposium on World-Wide Progress of the Petro Organic and Polymer Chemical Industries III. N. Platzer and S. Inoue Apr. 1979 Hawaii USA.*
"Database ZCAPLUS" Chemical Abstracts Service, XP002379859, Sep. 16, 1988.
Database Zcaplus, Chemical Abstracts Service, XP-002379859, pp. 1-2, Sep. 16, 1988.

* cited by examiner

*Primary Examiner*—Milton I Cano
*Assistant Examiner*—Aaron Greso
(74) *Attorney, Agent, or Firm*—Young & Thompson

(57) ABSTRACT

A compound of formula (I); its structure represented with dotted lines being either cis- or trans-double bonds wherein: A) $R_1$ represents a hydrogen atom and $R_2$ represents an OH, $OCH_3$ or $OC_2H_5$ group while either a) $R_4$, $R_5$, and $R_7$ each represent hydrogen atoms with $R_3$, $R_6$, and $R_8$ each representing methyl radicals; b) $R_4$, $R_6$, and $R_7$ each represent hydrogen atoms with $R_3$, $R_5$, and $R_8$ each representing methyl radicals; or c) $R_3$, $R_6$ and $R_7$ each represent hydrogen atoms with $R_4$, $R_5$, and $R_8$, each representing methyl radicals; or B) $R_7$ represents a hydrogen atom; $R_1$, $R_4$, and $R_6$ each represent hydrogen atoms with $R_2$, $R_3$, and $R_5$ each representing a methyl radical while $R_8$ represents OH, $OCH_3$ or $OC_2H_5$ groups when dotted lines are present; when dotted lines are absent, $R_8$ represents either $OCH_3$ or $OC_2H_5$ groups. At least one compound is applied as an odorant agent.

17 Claims, No Drawings

TRIMETHYLCYCLODODECATRIENE DERIVATIVES, USE THEREOF AND PERFUMED PRODUCTS CONTAINING THE SAME

This is a 371 PCT Application No. PCT/FR2006/000081, filed Jan. 13, 2006, claiming priority to application FR 0500550, filed Jan. 19, 2005.

The present invention relates in general to novel fragrant compounds that may be used in perfumery. The invention relates especially to novel alcohols and macrocyclic ethers, to a process for synthesizing them and to their use in perfumery as a result of their fragrancing properties.

The term "perfumery" is used herein to denote not only perfumery in the usual sense of the term, but also other fields in which the odor of products is important. They may be perfumery compositions in the usual sense of the term, such as fragrancing bases and concentrates, eaux de Cologne, eaux de toilette, perfumes and similar products; topical compositions—in particular cosmetic compositions—such as face and body creams, talcum powders, hair oils, shampoos, hair lotions, bath salts and oils, shower and bath gels, toiletry soaps, antiperspirants and body deodorants, shaving lotions and creams, soaps, creams, toothpastes, mouthwashes, pomades, and similar products; and maintenance products, such as laundry softeners, detergents, laundry washing products, ambient deodorants, and similar products.

The term "fragrant" is used herein to denote a compound that gives off an odor.

Macrocycles are already used in perfumery. In particular, the trimerization of isoprene results in a mixture of macrocyclic alkenes, which mainly contains two stereoisomers in varied ratios, especially 1,5,10-trimethylcyclododeca-1,5,9-triene and 1,5,9-trimethylcyclododeca-1,5,9-triene. This mixture of macrocycles provides the perfumery industry with a low-cost raw material. Certain derivatives, such as Cedroxyde™ (trimethyl-13-oxabicyclo[10.1.0]trideca-4,8-diene from Firmenich), Boisanol™ from Symrise or Trimofix™ O (2,5,10-trimethyl-2,5,9-cyclododecatrien-1-yl methyl ketone) from IFF, to name but a few, are commonly used.

Moreover, U.S. Pat. No. 3,723,478 from Firmenich describes the oxidation of certain trimethylcyclododecatrienes to ketone derivatives. The trimethylcyclododecadienones are obtained via an epoxidation, followed by opening of the epoxide and then oxidation. However, the yields for the steps of this synthetic route are low and the conversions are not very selective.

Consequently, there is still a need for novel fragrant macrocycles, and for a synthetic process whose yield and selectivity are improved.

The inventors have discovered, surprisingly, a novel process for synthesizing novel macrocycles, which have fragrant properties and which may thus be used in perfumery.

One subject of the present invention is thus a novel family of cyclic macromolecules represented by formula (I) below:

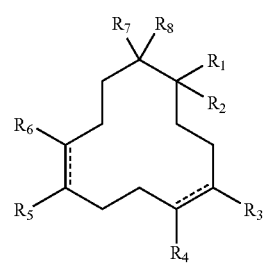

(I)

in which:

A)
a) $R_4$, $R_5$ and $R_7$ each represent a hydrogen atom and $R_3$, $R_6$ and $R_8$ each represent a methyl radical, or
b) $R_4$, $R_6$ and $R_7$ each represent a hydrogen atom and $R_3$, $R_5$ and $R_8$ each represent a methyl radical, or
c) $R_3$, $R_6$ and $R_7$ each represent a hydrogen atom and $R_4$, $R_5$ and $R_8$ each represent a methyl radical, and the dashed lines are present and represent cis or trans double bonds and $R_1$ represents a hydrogen atom and $R_2$ represents an —OH, —OCH$_3$ or —OC$_2$H$_5$ group, or the dashed lines are absent and $R_1$ represents a hydrogen atom and $R_2$ represents an —OCH$_3$ or —OC$_2$H$_5$ group, or B)
$R_1$, $R_4$ and $R_6$ each represent a hydrogen atom and $R_2$, $R_3$ and $R_5$ each represent a methyl radical, and the dashed lines are present and represent cis or trans double bonds and $R_7$ represents a hydrogen atom and $R_8$ represents an —OH, —OCH$_3$ or —OC$_2$H$_5$ group, or the dashed lines are absent and $R_7$ represents a hydrogen atom and $R_8$ represents an —OCH$_3$ or —OC$_2$H$_5$ group.

In particular, a subject of the invention is the novel compounds of formulae (5a-d), (6a-d) and (6a'-d') below,

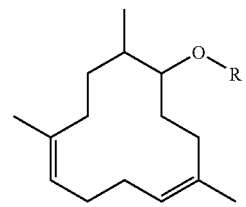

(a)

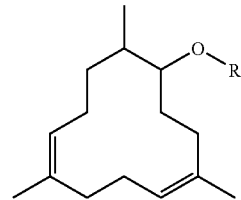

(b)

-continued

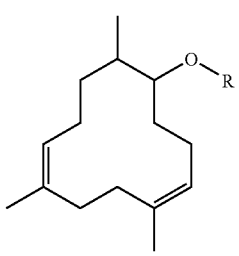
(c)

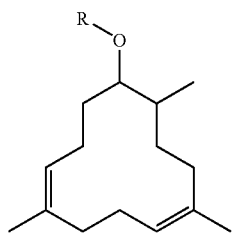
(d)

in which R is hydrogen atom (compounds 5a, 5b, 5c, 5d) or a methyl group (compounds 6a, 6b, 6c, 6d) or an ethyl group (compounds 6a', 6b', 6c', 6d').

Compounds 5a, 6a and 6a' are compounds of formula (I) in which $R_1$ represents a hydrogen atom, $R_2$ represents a group —OH (compound 5a), —OCH$_3$ (compound 6a) or —OC$_2$H$_5$ (compound 6a'), $R_3$ is a methyl group, $R_4$ is a hydrogen atom, $R_5$ is a hydrogen atom, $R_6$ is a methyl group, $R_7$ is a hydrogen atom, $R_8$ is a methyl group, and the double bonds are present.

Compounds 5b, 6b and 6b' are compounds of formula (I) in which $R_1$ represents a hydrogen atom, $R_2$ represents a group —OH (compound 5b), —OCH$_3$ (compound 6b) or —OC$_2$H$_5$ (compound 6b'), $R_3$ is a methyl group, $R_4$ is a hydrogen atom, $R_5$ is a methyl group, $R_6$ is a hydrogen atom, $R_7$ is a hydrogen atom, $R_8$ is a methyl group, and the double bonds are present.

Compounds 5c, 6c and 6c' are compounds of formula (I) in which $R_1$ represents a hydrogen atom, $R_2$ represents a group —OH (compound 5c), —OCH$_3$ (compound 6c) or —OC$_2$H$_5$ (compound 6c'), $R_3$ is a hydrogen atom, $R_4$ is a methyl group, $R_5$ is a methyl group, $R_6$ is a hydrogen atom, $R_7$ is a hydrogen atom, $R_8$ is a methyl group, and the double bonds are present.

Compounds 5d, 6d and 6d' are compounds of formula (I) in which $R_1$ represents a hydrogen atom, $R_2$ is a methyl group, $R_3$ is a methyl group, $R_4$ is a hydrogen atom, $R_5$ is a methyl group, $R_6$ is a hydrogen atom, $R_7$ is a hydrogen atom, $R_8$ represents a group —OH (compound 5d), —OCH$_3$ (compound 6d) or —OC$_2$H$_5$ (compound 6d'), and the double bonds are present.

In particular, a subject of the invention is also the novel compounds of formulae (7a-d) and (7a'-d') below:

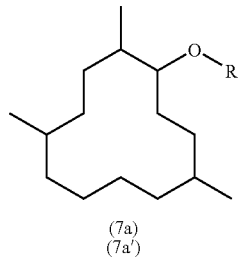
(7a)
(7a')

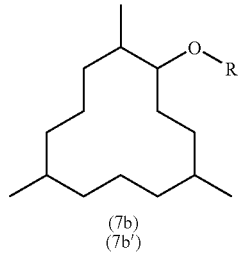
(7b)
(7b')

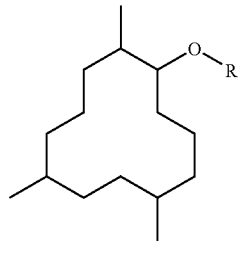
(7c)
(7c')

-continued

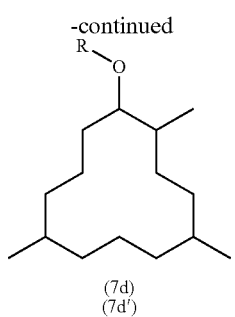

(7d)
(7d')

in which R is a methyl group (compounds 7a, 7b, 7c, 7d) or an ethyl group (compounds 7a', 7b', 7c', 7d').

Compounds 7a and 7a' are compounds of formula (I) in which $R_1$ represents a hydrogen atom, $R_2$ represents a group —$OCH_3$ (compound 7a) or —$OC_2H_5$ (compound 7a'), $R_3$ is a methyl group, $R_4$ is a hydrogen atom, $R_5$ is a hydrogen atom, $R_6$ is a methyl group, $R_7$ is a hydrogen atom, $R_8$ is a methyl group, and the double bonds are absent.

Compounds 7b and 7b' are compounds of formula (I) in which $R_1$ represents a hydrogen atom, $R_2$ represents a group —$OCH_3$ (compound 7b) or —$OC_2H_5$ (compound 7b'), $R_3$ is a methyl group, $R_4$ is a hydrogen atom, $R_5$ is a methyl group, $R_6$ is a hydrogen atom, $R_7$ is a hydrogen atom, $R_8$ is a methyl group, and the double bonds are absent.

Compounds 7c and 7c' are compounds of formula (I) in which $R_1$ represents a hydrogen atom, $R_2$ represents a group —$OCH_3$ (compound 7c) or —$OC_2H_5$ (compound 7c'), $R_3$ is a hydrogen atom, $R_4$ is a methyl group, $R_5$ is a methyl group, $R_6$ is a hydrogen atom, $R_7$ is a hydrogen atom, $R_8$ is a methyl group, and the double bonds are absent.

Compounds 7d and 7d' are compounds of formula (I) in which $R_1$ represents a hydrogen atom, $R_2$ is a methyl group, $R_3$ is a methyl group, $R_4$ is a hydrogen atom, $R_5$ is a methyl group, $R_6$ is a hydrogen atom, $R_7$ is a hydrogen atom, $R_8$ represents a group —$OCH_3$ (compound 7d) or —$OC_2H_5$ (compound 7d') and the double bonds are absent.

The compounds of formula (I) may be present in the form of an isomer or a mixture of isomers, in particular of an enantiomer and a mixtures of enantiomers, or of a racemic mixture, or of a diastereoisomer or mixture of diastereoisomers.

The compounds of formula (I) all have fragrant properties. Compounds (5a-d) have an amber, musk odor. Compounds (6a-d) and (6a'-d') have woody, camphor notes with a vetiver register. Compounds (7a-d) have fruity, green notes. As a result of these fragrant properties, these various products, most particularly the methyl ethers (6a-d), find very varied use, especially in perfumery.

A subject of the invention is thus also the use of these compounds as fragrant agents.

A subject of the present invention is also the process for synthesizing the compounds of formula (I).

Each of the compounds (5a-d), (6a-d), (6a'-d'), (7a-d) and (7a'-d') may be synthesized directly or indirectly from compounds (4a-d) below:

(4a)

(4b)

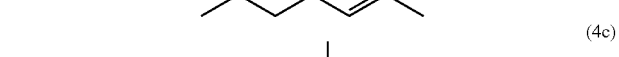

(4c)

-continued
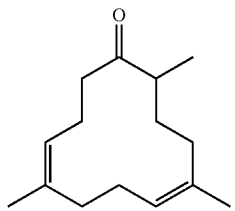
which themselves may be synthesized starting with trimethylcyclododecatrienes. The present invention also provides a novel process for preparing the macrocyclic ketones 4a-d, described below.
The scheme that follows shows a process for synthesizing the compounds according to the invention.
Scheme 1:
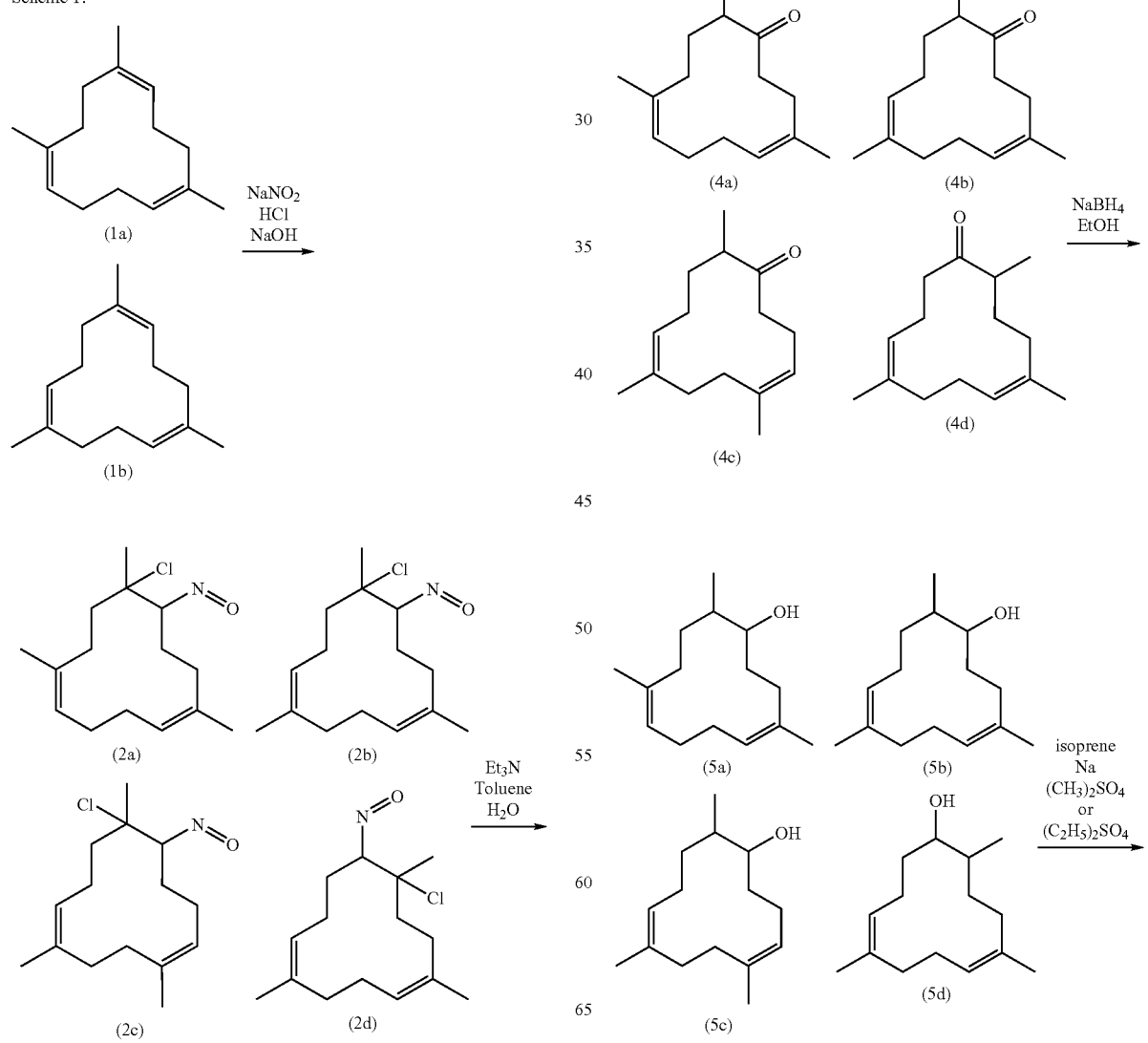
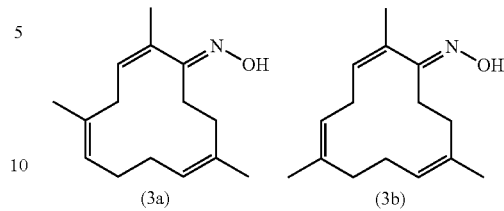

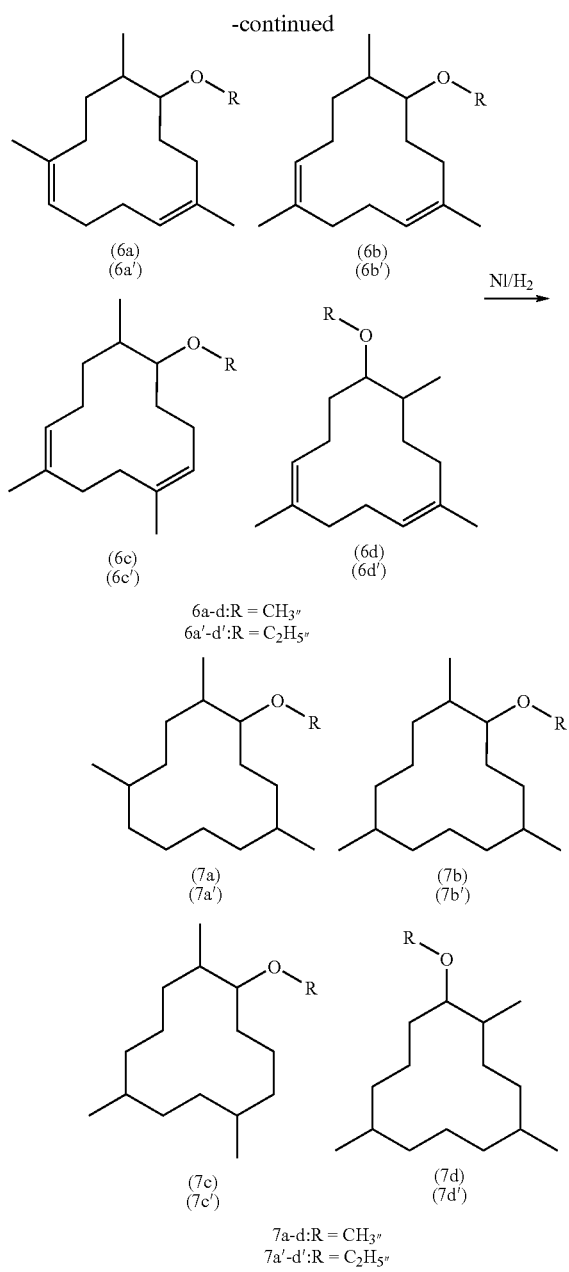

(6a)
(6a')

(6b)
(6b')

(6c)
(6c')

(6d)
(6d')

6a-d: R = CH$_3$″
6a'-d': R = C$_2$H$_5$″

(7a)
(7a')

(7b)
(7b')

(7c)
(7c')

(7d)
(7d')

7a-d: R = CH$_3$″
7a'-d': R = C$_2$H$_5$″

Ni/H$_2$

In general, the process according to the invention comprises the following steps:
- formation of chloro-nitroso derivatives from 1,5,10-trimethylcyclododeca-1,5,9-triene (1a) and from 1,5,9-trimethylcyclododeca-1,5,9-triene (1b),
- conversion of these derivatives into oximes,
- reductive conversion of the oximes into ketones in the presence of Raney nickel, acetone and boric acid,
- reduction of the ketones to alcohols,
- etherification to ethers,
- optionally, hydrogenation to saturated ethers.

In a first stage, the chloro-nitroso derivatives (2a-d) of 1,5,10-trimethylcyclododecatriene (1a) and 1,5,9-trimethylcyclododecatriene (1b) are formed. A large number of reagents, known to those skilled in the art, are available for this reaction and allow the expected result to be achieved. Among these reagents, sodium nitrite is advantageous for economic reasons. The trimethylcyclododecatrienes (1a-b) are cooled, in a solvent such as sec-butanol, to a temperature of about −10° C. to −20° C., since the reaction is highly exothermic. Sodium nitrite (the reagent used in this embodiment) is then added portionwise, while hydrochloric acid is added dropwise in parallel. White crystals form. After the end of addition of the reagents, the reaction medium is stirred for a further 16 hours while allowing the bulk temperature to return to room temperature. Next, the solution is neutralized with cooling, such that the bulk temperature does not exceed 25° C., with sodium hydroxide or another suitable base. The chloro-nitroso derivatives (2a-d) are obtained in the form of crystals, which are washed, filtered and dried, and may be used directly in the following step.

Next, the chloro-nitroso derivatives (2a-d) are converted into oximes (3a-d), under suitable conditions that a person skilled in the art can determine given his general knowledge. The conversion into oximes is preferably performed in an aqueous medium in the presence of a base. The use of several bases may be envisaged, but a good yield is obtained in the presence of triethylamine. The crystals (2a-d) are suspended in a mixture of water, toluene and triethylamine. The suspension is refluxed for about four to six hours. Total disappearance of the crystals indicates total conversion. After cooling, the phases are separated and the organic phase is washed until neutral with brine, then with sulfuric acid and again with brine. After concentrating the solvent, the oximes (3a-d) are obtained in the form of a brown mass, which may be used directly in the following reaction, since purification is possible but difficult given the molecular mass and the complexity of the crude product.

There is a wide variety of oxidizing and reducing methods for converting an oxime into a ketone, which are known to those skilled in the art, and several reagents may be used to obtain ketones, for instance sodium bisulfite, copper sulfate, sodium nitrite, levulinic acid and oxone, to name but a few. In the present case, all these attempts failed. Only the reductive conversion in the presence of Raney nickel, acetone/ethanol and boric acid made it possible to obtain ketones (4a-d). To do this, the oximes (3a-d) were partially dissolved in a mixture of ethanol and acetone and were placed in an autoclave in the presence of Raney nickel and boric acid. The reaction medium is then stirred for about 14 hours at a temperature of about 25° C. to 60° C. and a hydrogen pressure of about $1\times10^4$ HPa to $5\times10^4$ HPa, which makes it possible to obtain the ketones (4a-d); i.e. 4,9,12-trimethylcyclododeca-4,8-dienone (4a); 4,8,12-trimethylcyclododeca-4,8-dienone (4b), 5,8,12-trimethylcyclododeca-4,8-dienone (4c); 5,9,12-trimethylcyclododeca-4,8-dienone (4d).

The solution is then cooled to room temperature, quenched in water and extracted with a solvent, for instance toluene. The combined organic phases are washed until neutral, dried, concentrated and then distilled. The mixture of ketones (4a-d) has a musk, flowery and slightly woody odor.

Reduction of the ketones (4a-d) to alcohols (5a-d) may be performed under suitable conditions that a person skilled in the art can determine. In particular, the reduction in ethanol may be performed using sodium borohydride, which is preferred to other suitable reagents for its ease of use and its reasonable price. The sodium borohydride is added to the alcoholic solution over a period of about 36 hours at a temperature of about 5° C. to 15° C. The excess hydride is destroyed with acetone. After acidification with hydrochloric acid, the solution is quenched with water and then extracted. The combined organic phases are washed until neutral, dried, filtered and concentrated. After distillation, alcohols (5a-d) are obtained.

These alcohols have an amber, musk odor, which is relatively faint but definite.

The alcohols may then be etherified under suitable conditions known to those skilled in the art. Two classes of reagents are generally used for the etherification of alcohols: alkyl halides and alkyl sulfates. The two classes of reagents may be used to obtain the ethers (6a-d and 6a'-d'). For economic reasons, dimethyl sulfate and diethyl sulfate are preferred. In order to facilitate the formation of the alkoxides, isoprene is added dropwise to the solution of the trimethylcyclododecadienols (5a-d) in tetrahydrofuran, in which pieces of sodium are suspended. The sodium reacts first with the isoprene, forming a cation that then reacts rapidly with the alcohols present. This reaction is performed at a temperature of about 10° C. to 20° C. Once all the sodium has reacted, the etherification reagent (for example dimethyl or diethyl sulfate) is added. The reaction medium is refluxed for about six hours. The reaction is complete once the solution has become colorless. Aqueous ammonia solution is added with cooling (10° C. to 20° C.) to destroy the excess sulfate. The aqueous phase is extracted with a solvent such as t-butyl methyl ether. The combined organic phases are washed until neutral, dried, filtered and concentrated. Distillation gives the methyl ethers (6a-d) or the ethyl ethers (6a'-d'), which are novel compounds. The methyl ethers (6a-d) have woody, camphor notes with a vetiver register, which are highly appreciated by perfumers. The ethyl ethers (6a'-d') have more or less the same notes as the methyl ethers (6a-d), while at the same time being much less volatile.

The ethers (6a-d) may then be hydrogenated to obtain the corresponding saturated ethers (7a-d), under conditions that may be determined by a person skilled in the art. In particular, the hydrogenation may be performed in the presence of palladium-on-charcoal, for example, at a temperature of about 20° C. to 80° C., under a pressure of about $2 \times 10^4$ HPa to $8 \times 10^4$ HPa of hydrogen. The ethers obtained are novel compounds. They have fleeting fruity, green notes.

The process described above makes it possible to obtain each group of compounds 4, 5, 6 and 7 in the form of a mixture a-d or a'-d'. It is difficult but possible to separate the compounds of a mixture, via suitable techniques known to those skilled in the art, in particular via separation on a chiral column or preparative chromatography. Given these difficulties, it is not absolutely necessary to separate them, and the compounds may also be used as a mixture, since each mixture itself has fragrant properties.

A subject of the invention is also the use of at least one compound of formula (I) according to the invention as a fragrant agent, as an odor-masking agent or as an odor-neutralizing agent, alone or as a mixture with one or more other fragrant compounds known to those skilled in the art, which a person skilled in the art is capable of selecting as a function of the desired effect. The additional fragrant agent(s) may be compounds of formula (I) or other fragrant agents known to those skilled in the art.

A subject of the invention is also compositions comprising a base product and an effective amount of one or more compounds of formula (I) according to the invention.

It may be a composition that is itself fragrant, or a composition in which the fragrant agent is used to mask or neutralize certain odors.

The base product will readily be determined by a person skilled in the art as a function of the intended composition and thus of the intended use, for which the usual components, such as solvent(s) and/or adjuvant(s), are well known.

The effective amount of the compounds of formula (I) according to the invention incorporated into the composition will vary according to the nature of the composition, the desired fragrancing effect, and the nature of the other fragrant or non-fragrant compounds that may be present, and may be readily determined by a person skilled in the art, given that it may vary within a very wide range, from 0.1% to 99% by weight, in particular 0.1% to 50% by weight and especially 0.1% to 30% by weight.

The compounds of formula (I) according to the invention may be used in unmodified form or may be incorporated into or onto a support material that is inert or that may contain other active ingredients of the finished composition. A wide variety of support materials may be used, including, for example, polar solvents, oils, greases, finely divided solids, cyclodextrins, maltodextrins, gums, resins and any other support material known for such compositions.

A subject of the invention is thus also the use of the compounds of formula (I) for the preparation of a fragrant composition or of a fragrant article in the applications described above, in particular in perfumery, in cosmetics, for example for shampoos or soaps, or for maintenance products, such as laundry softeners or laundry washing products.

The invention relates in particular to a perfumery composition, especially a fragrant base or concentrate, an eau de Cologne, an eau de toilette or a fragrance, comprising at least one compound of formula (I) or a compound comprising at least one compound of formula (I).

The invention also relates in particular to a cosmetic composition, especially face or body cream, talcum powder, hair or body oil, shampoo, hair lotion, bath salt, bath oil, shower gel, bath gel, toiletry soap, body antiperspirant, body deodorant, lotions, shaving cream, shaving soap, cream, toothpaste, mouthwash or pomade comprising at least one compound of formula (I) or at least one composition comprising at least one compound of formula (I). Another subject of the invention is a preventive or non-preventive cosmetic treatment or care method, using at least one compound of formula (I) or at least one composition comprising at least one compound of formula (I).

The invention also relates to a maintenance product, especially laundry softener, detergent, laundry washing product or ambiance deodorizer, comprising at least one compound of formula (I) or at least one composition comprising at least one compound of formula (I).

The compounds according to the invention may be used, alone or in combination, in unmodified form or may be incorporated into or onto a support material that is inert or that may contain other active ingredients of the finished composition. A wide variety of support materials may be used, including, for example, polar solvents, oils, greases, finely divided solids, cyclodextrins, maltodextrins, gums, resins and any other support material known for such compositions.

A subject of the invention is thus also the use of the novel compounds for the preparation of a fragrant composition or of a fragrant article in the applications described above, in particular in perfumery, in cosmetics, for example for shampoos or soaps, and for maintenance products, such as softeners or laundry washing products.

The invention relates in particular to a perfumery composition, especially a fragrant base or concentrate, an eau de Cologne, an eau de toilette or a fragrance, comprising at least one compound of formula (I) or a composition comprising at least one compound of formula (I).

The invention also relates in particular to a cosmetic composition, especially face or body cream, talcum powder, hair or body oil, shampoo, hair lotion, bath salt, bath oil, shower gel, bath gel, toiletry soap, body antiperspirant, body deodorant, lotions, shaving cream, shaving soap, cream, toothpaste, mouthwash or pomade, comprising at least one compound of formula (I) or a composition comprising at least one compound of formula (I). Another subject of the invention is a preventive or non-preventive cosmetic treatment or care method, using at least one compound of formula (I) or at least one composition comprising at least one compound of formula (I).

The examples that follow further illustrate the various processes for manufacturing the already-known or novel molecules according to the invention, and also the use and value thereof. These examples are given for purely illustrative purposes and should not be considered as limiting the invention.

EXAMPLE 1

Synthesis of the chlorotrimethylnitrosocyclododecadienes (2a-d)

408.0 g (2.00 mol) of trimethylcyclododecatrienes (1a and b) and 700.0 g of sec-butanol are placed in a four-liter round-bottomed flask equipped with a side tube with a powder funnel, a dropping funnel and a thermometer. The solution is cooled to between −10° C. and −15° C. 640.0 g (6.00 mol) of 34% hydrochloric acid are added dropwise over a period of about six hours, with simultaneous portionwise addition of 160.0 g (2.32 mol) of sodium nitrite. The reaction is highly exothermic. Efficient cooling is recommended so as not to exceed 0° C. in the bulk. The reaction medium is stirred for a further sixteen hours while allowing the bulk temperature to return to room temperature. Gray-white crystals form and the reaction medium becomes pasty. Next, 1000.0 g of water are added to facilitate the stirring. The mixture is cooled again and 300.0 g (3.53 mol) of 47% sodium hydroxide are added dropwise without exceeding 25° C. in the bulk. The crystals are filtered off, rinsed with 325.0 g of hexane and screened (1.25 screen). The crystals are dried under vacuum (first at 40 HPa and then at 0.7 HPa). 419.7 g (max. 1.56 mol) of chlorotrimethylnitrosocyclododecadienes (2a-d) are obtained, which contain traces of starting material and which are virtually insoluble in all the solvents tried. The yield is maximal at 78.0%. The crystals are used directly in the following step.

EXAMPLE 2

Synthesis of the trimethylcyclododecatrienone oximes (3a-d)

270.0 g (1.00 mol) of chlorotrimethylnitrosocyclododecadienes (2a-d), 301.0 g of toluene and 121.5 g (1.20 mol) of trimethylamine are placed in a two-liter round-bottomed flask equipped with a condenser, a dropping funnel and a thermometer, and the mixture is brought to 60° C. 350.0 ml of water are added dropwise at this temperature and the reaction medium is then refluxed (at about 80° C.) with vigorous stirring for four hours. The reaction medium is cooled to 60° C. and the aqueous phase is separated out. The organic phase is then washed twice with 200 ml of brine, once with 250 ml of 10% sulfuric acid and then once again with 200 ml of brine. The solvent is concentrated under reduced pressure (about 40 HPa), without exceeding 50° C. in the bulk. 228.00 g of a pasty brown mass are obtained, and are used directly in the following step.

EXAMPLE 3

Synthesis of the trimethylcyclododecadienones (4a-d)

78.0 g of ethanol, 158.0 g (2.72 mol) of acetone, 2.3 g (0.04 mol) of boric acid, 30.0 g (1.67 mol) of water, 4.0 g of Raney nickel and 228.0 g of crude trimethylcyclododecatrienone oximes (3a-d) are placed in an 800 ml autoclave. The apparatus is flushed three times with hydrogen. The mixture is stirred for 24 hours at 50° C. and a hydrogen pressure of $3 \times 10^4$ HPa. The apparatus is cooled to room temperature and the reaction medium is recovered. 500 ml of toluene and then 300 ml of brine are added. The phases are separated and the aqueous phase is extracted once with 100 ml of toluene. The combined organic phases are washed six times with 100 ml of 10% hydrochloric acid to neutral pH. The resulting organic phase is washed once more with 100 ml of brine and then dried, filtered and concentrated under vacuum (40 HPa) without exceeding 50° C. in the bulk. After distillation, 124.8 g (0.57 mol) of trimethylcyclododecadienones (4a-d) are obtained (b.p.: 94-97° C./0.3 HPa). The yield for the two steps is 57%. The infrared, NMR and mass spectrum analyses correspond to the structures of the expected compounds.

EXAMPLE 4

Synthesis of Trimethylcyclododecadienols (5a-d)

124.8 g (0.57 mol) of trimethylcyclododecadienones (4a-d) and 390.0 g of ethanol are placed in a two-liter round-bottomed flask equipped with a thermometer. The mixture is cooled to 5° C. and 10.7 g of sodium borohydride are added portionwise without exceeding 10° C. in the bulk. The mixture is stirred at this temperature for 42 hours. Additional amounts of sodium borohydride are added during this period (5.3 g after six hours, 10.1 g after 24 hours and 5.3 g after 36 hours; total amount of sodium borohydride used: 31.4 g (0.863 mol)). 79.0 g (1.36 mol) of acetone are added dropwise to destroy the excess reducing agent, without exceeding 10° C. in the bulk. The reaction mixture is acidified with 500.0 g of 10% hydrochloric acid, without exceeding 10° C. in the bulk. A further 800 g of water and then 344 g of toluene are added with vigorous stirring. The phases are separated and the organic phase is washed three times with 200 g of water and once with 200 g of brine. The resulting organic phase is dried and filtered, and the toluene is evaporated off under reduced pressure (40 HPa) without exceeding 50° C. in the bulk. After distillation, 69.6 g (0.31 mol) of trimethylcyclododecadienes (5a-d) are obtained (b.p.: 98-100° C./0.2 HPa). The yield is 55.3%. The infrared, NMR and mass spectrum analyses correspond to the structures of the expected compounds.

EXAMPLE 5

Synthesis of the methoxytrimethylcyclododecadienes (6a-d)

360.0 g of tetrahydrofuran, 69.6 g (0.31 mol) of trimethylcyclododecadienols (5a-d) and 8.2 g (0.36 mol) of sodium, chopped into small pieces, are placed in a two-liter round-bottomed flask equipped with a condenser, a thermometer and a dropping funnel. The reaction medium is cooled to 15° C. and 41.6 ml (28.3 g, 0.42 mol) of isoprene are added dropwise, without exceeding 15° C. in the bulk. Stirring is continued until the sodium has completely dissolved. The mixture is cooled to 10° C. and 33.8 ml (45.0 g, 0.357 mol) of dimethyl sulfate are added dropwise at this temperature. The reaction medium is refluxed for 6 hours until the solution has totally decolorized. The resulting solution is cooled to 10° C. and 300 ml of aqueous 10% ammonia solution are added dropwise, without exceeding 15° C. in the bulk. The phases are separated and the aqueous phase is extracted twice with 150 ml of t-butyl methyl ether. The combined organic phases are washed once with 150 g of 10% hydrochloric acid, twice with 150 g of water and then once with 150 g of brine. The resulting organic phase is dried and filtered, and the solvents are evaporated off under vacuum (40 HPa), without exceeding 50° C. in the bulk. After distillation, 33.5 g (0.14 mol) of methoxy-trimethylcyclododecadienes (6a-d) are obtained (b.p.: 68-72° C./0.2 HPa). The yield is 45.7%. The infrared, NMR and mass spectrum analyses correspond to the structures of the expected compounds.

EXAMPLE 6

Synthesis of the ethoxytrimethylcyclododecadienes (6a'-d')

The ethoxytrimethylcyclododecadienes (6a'-d') are synthesized as described in Example 4, using 28.9 g (0.12 mol) of trimethylcyclododecadienes (5a-d) and 20.4 g (0.36 mol) of diethyl sulfate. 18.2 g (0.07 mol) of ethoxytrimethylcyclododecadienes (6a'-d') are obtained (b.p.: 105/108° C./0.2 HPa). The yield is 62.7%. The infrared, NMR and mass spectrum analyses correspond to the structures of the expected compounds.

EXAMPLE 7

Synthesis of the methoxytrimethylcyclododecanes (7a-d)

7.6 g (32 mmol) of methoxytrimethylcyclododecadienes (6a-d), 100 ml of ethanol and 0.5 g of palladium-on-charcoal are placed in an autoclave. The apparatus is closed and flushed three times with hydrogen. The mixture is stirred for six hours at 40° C. and $4 \times 10^4$ HPa of hydrogen, and then cooled to room temperature and the reaction medium is recovered. The catalyst is filtered off and the solvent is evaporated off under reduced pressure (40 HPa), without exceeding 50° C. in the bulk. After micro-distillation, 5.0 g (20.8 mmol) of methoxytrimethylcyclododecanes (7a-d) are obtained (71-78° C./0.3 HPa). The yield is 65.0%. The infrared, NMR and mass spectrum analyses correspond to the structures of the expected compounds.

EXAMPLE 8

Olfactory Evaluation

In a first stage, the fragrance characteristics of the pure methoxytrimethylcyclododecadienes (6a-d) were evaluated by a panel at the same time as the fragrance characteristics of known, commercially available compounds. The evaluation panel is composed of several professionals, who evaluate each compound qualitatively and quantitatively. The mixture of compounds was described as woody, camphoric, in the vetiver register and very strong. Analogies were found with certain commercially available products, for instance Spirambrene™ (2,2,3',7',7-pentamethylspiro-1,3-dioxane-5,2'-norcarane) from Givaudan, Karanal™ (5-sec-butyl-2-(2,4-dimethylcyclohex-3-enyl)-5-methyl[1,3]dioxane) from Quest International, Cedramber™ (6-methoxy-3,6,8,8-tetramethyloctahydro-3a,7-methanoazulene) from International Flavours and Fragrances, or Boisambrene™ (ethoxymethoxycyclododecane) from Henkel.

Next, two alcoholic compositions were produced, in which the mixture of methoxytrimethylcyclododecadienes (6a-d) was compared with commercial products. In each case, the evaluations of the olfactory impact were made at $t_0$, $t_{+48h}$ and $t_{+168h}$ to evaluate the head, core and base notes, in comparison with known compounds.

| | Composition 1 | | |
|---|---|---|---|
| Component | Test 1 % (by weight) | Test 2 % | Test 3 % |
| Crystalline cedryl acetate[1] | 0.80 | 0.80 | 0.80 |
| Linalyl acetate | 1.00 | 1.00 | 1.00 |
| Haiti vetiveryl acetate | 4.50 | 4.50 | 4.50 |
| Trans-anethole | 0.30 | 0.30 | 0.30 |
| Orcanox[2] | 0.40 | 0.40 | 0.40 |
| Bergamot Ess. | 0.60 | 0.60 | 0.60 |
| Sweet orange Ess. | 0.30 | 0.30 | 0.30 |
| Cashmeran[3] | 0.70 | 0.70 | 0.70 |
| Galaxolide[4] | 20.00 | 20.00 | 20.00 |
| Methyl dihydrojasmonate[5] | 6.00 | 6.00 | 6.00 |
| Iso E Super[6] | 52.00 | 52.00 | 52.00 |
| Linalool | 0.50 | 0.50 | 0.50 |
| Brazil orange terpenes | 0.10 | 0.10 | 0.10 |
| Haiti vetiver Ess. | 1.00 | 1.00 | 1.00 |
| Haiti vetiverol[1] | 1.00 | 1.00 | 1.00 |
| 10% isoeugenyl acetate in DPG[7] | 0.10 | 0.10 | 0.10 |
| Cardamom Ess. | 0.40 | 0.40 | 0.40 |
| Pure citral from Litsea cubeba at 10% in DPG[7] | 0.30 | 0.30 | 0.30 |
| Cedramber[8] | 10.00 | / | / |
| Boisambrene[9] | / | / | 10.00 |
| Methoxytrimethylcyclododecadiene (6a-d) | / | 10.00 | / |
| Total | 100.00 | 100.00 | 100.00 |

[1]Origin: V. Mane Fils, France
[2]3a,6,6,9a-Tetramethyldodecahydronaphtho[2,1-b]-furan; origin: V. Mane Fils, France.
[3]1,1,2,3,3-Pentamethyl-1,2,3,5,6,7-hexahydroinden-4-one; origin: International Flavours and Fragrances, USA.
[4]1,1,2,3,3,8-Hexamethyl-1,2,3,5,7,8-hexahydro-6-oxacyclopenta[b]naphthalene; origin: International Flavours and Fragrances, USA.
[5][3-Oxo-2-((E)-pentyl)cyclopentyl]acetic acid methyl ester; origin: Firmenich, Switzerland.
[6]1-(2,3,8,8-Tetramethyl-1,2,3,4,5,6,7,8-octahydro-naphthalen-2-yl)ethanone; origin: International Flavours and Fragrances, USA.
[7]Dipropylene glycol.
[8]6-Methoxy-3,6,8,8-tetramethyloctahydro-3a,7-methanoazulene; origin: International Flavours and Fragrances, USA.
[9]Ethoxymethoxycyclododecane; origin: Henkel, Germany

| | Composition 2 | | |
|---|---|---|---|
| Material used | Test 4 Parts (by weight) | Test 5 Parts | Test 6 Parts |
| Violettine[1] | 5 | 5 | 5 |
| Orcanox[2] | 20 | 20 | 20 |
| Calon 1951 Cal[3] | 5 | 5 | 5 |
| Veramoss[4] | 2 | 2 | 2 |
| Ethyl linalool[5] | 50 | 50 | 50 |
| Florol[6] | 10 | 10 | 10 |
| Methyl dihydrojasmonate[7] | 287 | 287 | 287 |
| Helional[8] | 30 | 30 | 30 |
| Iso E Super[9] | 20 | 20 | 20 |
| Lilial[10] | 10 | 10 | 10 |
| Melonal[11] | 1 | 1 | 1 |

-continued

Composition 2

| Material used | Test 4 Parts (by weight) | Test 5 Parts | Test 6 Parts |
|---|---|---|---|
| Methylionanthene[12] | 5 | 5 | 5 |
| Benzyl salicylate | 10 | 10 | 10 |
| Cis-3-hexenyl acetate[13)14] | 2 | 2 | 2 |
| Styrallyl acetate[14] | 5 | 5 | 5 |
| Allyl amyl glycolate[14] | 1 | 1 | 1 |
| Galbex[15] | 2 | 2 | 2 |
| Cis-3-hexenol[14] | 2 | 2 | 2 |
| Liffarome[16] | 2 | 2 | 2 |
| Triplal[14)17] | 1 | 1 | 1 |
| Methoxytrimethylcyclododecadiene (6a-d) | / | 30 | / |
| Strong Boisambrene[18] | / | / | 30 |
| Total | 470 | 500 | 500 |

[1] (E)-Undeca-1,3-dien-5-yne; origin: Firmenich, Switzerland
[2] 3a,6,6,9a-Tetramethyldodecahydronaphtho[2,1-b]-furan; origin: V. Mane Fils, France.
[3] 7-Methylbenzo[b][1,4]dioxepin-3-one; origin; Symrise, Germany
[4] 2,4-Dihydroxy-3,6-dimethylbenzoic acid methyl ester; origin: International Flavours and Fragrances, USA.
[5] Origin: Givaudan, Switzerland.
[6] 2-Isobutyl-4-methyltetrahydropyran-4-ol; origin: Firmenich, Switzerland.
[7] [3-Oxo-2-((E)-pentyl)cyclopentyl]acetic acid methyl ester; origin: Firmenich, Switzerland.
[8] 3-Benzo[1,3]dioxol-5-yl-2-methylpropionaldehyde; origin: International Flavours and Fragrances, USA.
[9] 1-(2,3,8,8-Tetramethyl-1,2,3,4,5,6,7,8-octahydro-naphthalen-2-yl)ethanone; origin: International Flavours and Fragrances, USA.
[10] 3-(4-tert-Butylphenyl)-2-methylpropionaldehyde: origin: Givaudan, Switzerland.
[11] 2,6-Dimethylhept-5-enal; origin: Guivaudan Switzerland.
[12] (E)-3-Methyl-4-(2,6,6-trimethylcyclohex-2-enyl)-but-3-en-2-one; origin; Firmenich, Switzerland.
[13] Origin: V. Mane Fils, France.
[14] 10% in dipropylene glycol.
[15] Origin: Firmenich, Switzerland.
[16] Carbonic acid (E)-hex-3-enyl ester methyl ester; origin: International Flavours and Fragrances, USA.
[17] 2-4-Dimethylcyclohex-3-enecarbaldehyde; origin: International Flavours and Fragrances, USA.
[18] Ethoxymethoxycyclododecane; origin: Henkel, Germany.

The tests of composition 1 showed that the methoxytrimethylcyclododecadienes (6a-d) are free of the amber note of Boisambrene™ but are, on the other hand, more powerful than Boisambrene™ in their woody notes and as a result have a similar impact to that of Cedramber™.

The tests of composition 2 confirmed that the methoxytrimethylcyclododecadienes (6a-d) are less ambery and less rising than Boisambrene™, but, on the other hand, are deeper in the base notes and give cedar wood, honey and waxy hints.

Furthermore, the loss of intensity over time appears relatively linear in all cases, without revealing a substantial change in fragrance characteristic.

The results of these evaluations show without the slightest doubt that the mixture of compounds described above has advantageous fragrance characteristics, which will find an application in particular in perfumery.

The invention claimed is:

1. A compound of general formula (I) below:

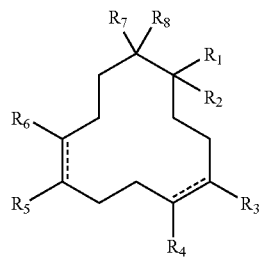

(I)

in which:

A)

a) $R_4$, $R_5$ and $R_7$ each represent a hydrogen atom and $R_3$, $R_6$ and $R_8$ each represent a methyl radical, or b) $R_4$, $R_6$ and $R_7$ each represent a hydrogen atom and $R_3$, $R_5$ and $R_8$ each represent a methyl radical, or c) $R_3$, $R_6$ and $R_7$ each represent a hydrogen atom and $R_4$, $R_5$ and $R_8$ each represent a methyl radical, and the dashed lines are present and represent cis or trans double bonds and $R_1$ represents a hydrogen atom and $R_2$ represents an —$OCH_3$ or —$OC_2H_5$ group, or the dashed lines are absent and $R_1$ represents a hydrogen atom and $R_2$ represents an —$OCH_3$ or —$OC_2H_5$ group, or

B)

$R_1$, $R_4$ and $R_6$ each represent a hydrogen atom and $R_2$, $R_3$ and $R_5$ each represent a methyl radical, and the dashed lines are present and represent cis or trans double bonds and $R_7$ represents a hydrogen atom and $R_8$ represents an —$OCH_3$ or —$OC_2H_5$ group, or the dashed lines are absent and $R_7$ represents a hydrogen atom and $R_8$ represents an —$OCH_3$ or —$OC_2H_5$ group, said compound being an ether derivative.

2. The compound as claimed in claim 1, corresponding to one of the following formulae:

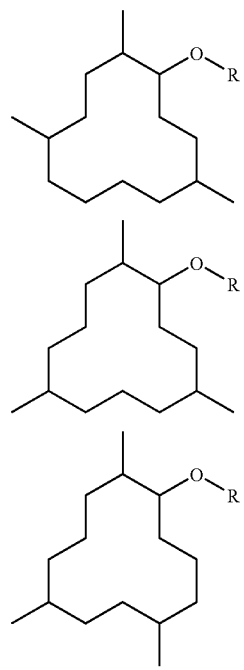

-continued

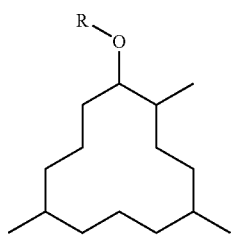

in which R is a methyl group or an ethyl group.

3. The compound as claimed in claim 1, corresponding to one of the following formulae:

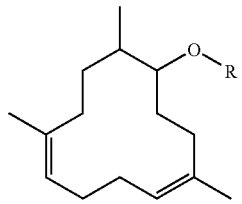

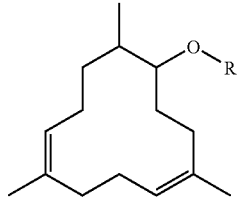

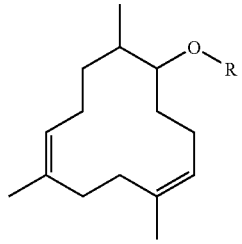

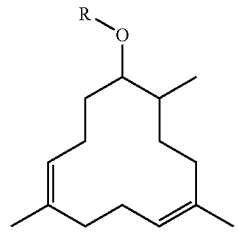

in which R is a methyl group or an ethyl group.

4. A composition, characterized in that it contains at least one compound of formula (I), of claim 1 to 3, in the form of an isomer or a mixture of isomers, in particular of an enantiomer or a mixture of enantiomers, or of a racemic mixture, or of a diastereoisomer or mixture of diastereoisomers.

5. The composition as claimed in claim 4, characterized in that it contains a mixture of at least two compounds chosen from compounds 6a, 6b, 6c and/or 6d:

(6a)
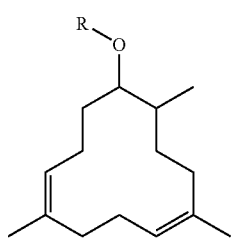

(6b)
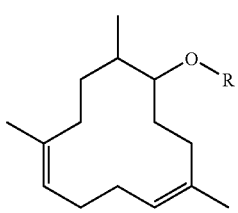

(6c)
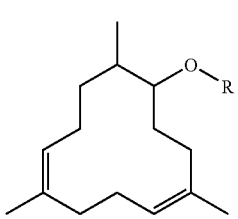

(6d)
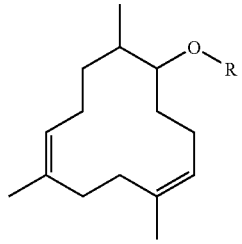

in which R is a methyl group.

6. The composition as claimed in claim 4, characterized in that it contains a mixture of at least two compounds chosen from compounds 6a', 6b', 6c' and/or 6d':

(6a')
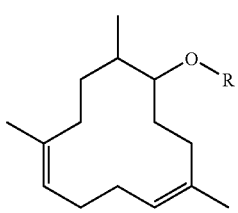

(6b')
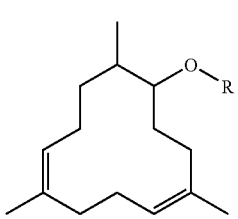

-continued

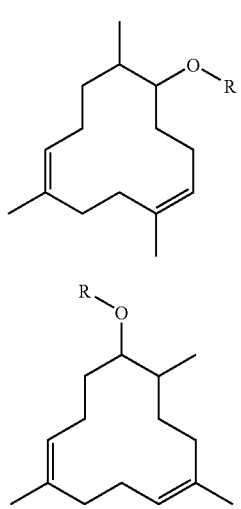

(6c')

(6d')

in which R is an ethyl group.

7. The composition as claimed in claim 4, characterized in that it contains a mixture of at least two compounds chosen from compounds 7a, 7b, 7c and/or 7d:

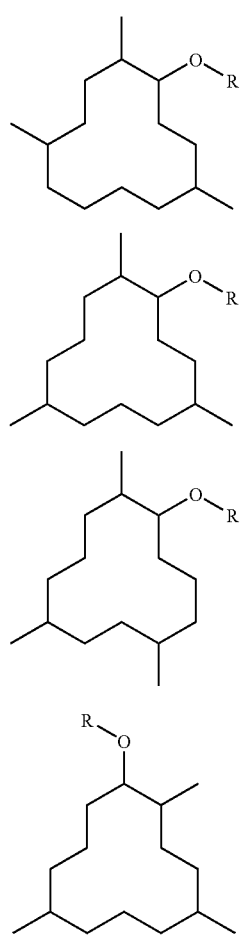

(7a)

(7b)

(7c)

(7d)

in which R is a methyl group.

8. The composition as claimed in claim 4, characterized in that it contains a mixture of at least two compounds chosen from compounds 7a', 7b', 7c' and/or 7d':

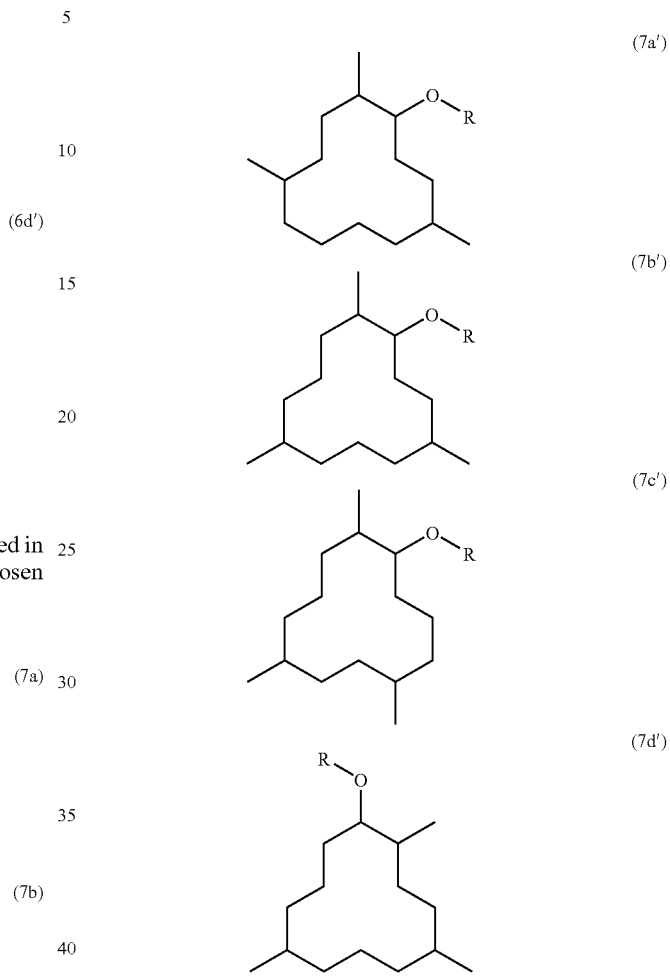

(7a')

(7b')

(7c')

(7d')

in which R is an ethyl group.

9. The composition as claimed in claim 4, characterized in that said compound(s) of formula (I) is (are) incorporated into or onto a support material that is inert or that may contain other active ingredients, said support especially being chosen from polar solvents, oils, greases, finely divided solids, cyclodextrins, maltodextrins, gums and resins.

10. A perfumery composition, especially a fragrant base or concentrate, eau de Cologne, eau de toilette or fragrance, characterized in that it comprises at least one compound of claim 1.

11. A perfumery composition characterized in that it comprises at least one composition as of claim 5.

12. A cosmetic composition, especially a face or body cream, talcum powder, hair or body oil, shampoo, hair lotion, bath salt, bath oil, shower gel, bath gel, toiletry soap, body antiperspirant, body deodorant, lotions, shaving cream, shaving soap, cream, toothpaste, mouthwash or pomade, characterized in that it comprises at least one compound of claim 1.

13. A maintenance product, especially laundry softener, detergent, laundry washing product or ambiance deodorant, characterized in that it comprises at least one compound of claim 1.

14. The composition as claimed in claim 4, comprising a mixture of the four compounds 6a, 6b, 6c and 6d below:

(6a)
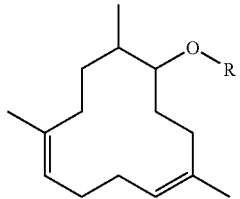

(6b)
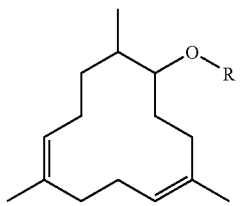

(6c)
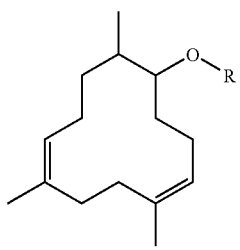

(6d)
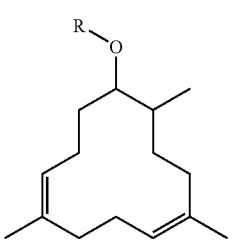

in which R is a methyl group.

15. The composition as claimed in claim 4, comprising a mixture of the four compounds 6a', 6b', 6c' and 6d' below:

(6a')
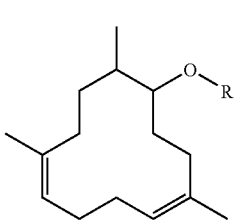

(6b')
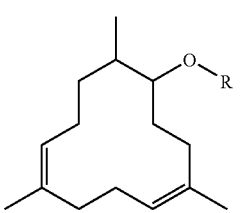

-continued (6c')
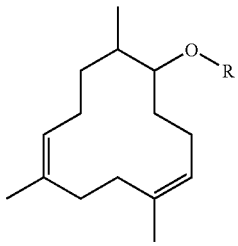

(6d')
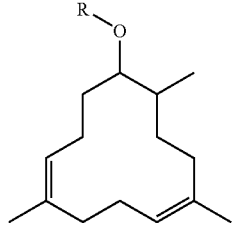

in which R is an ethyl group.

16. The composition as claimed in claim 4, comprising a mixture of the four compounds 7a, 7b, 7c and/or 7d below:

(7a)
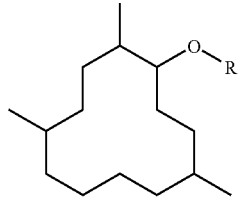

(7b)
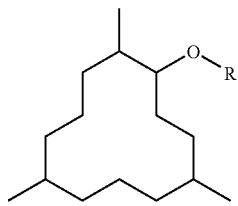

(7c)
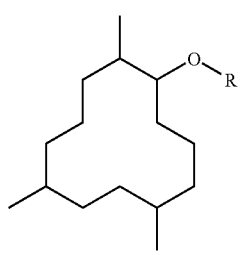

(7d)
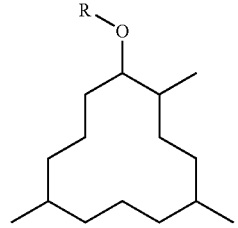

in which R is a methyl group.

17. The composition as claimed in claim 4, comprising a mixture of the four compounds 7a', 7b', 7c' and/or 7d' below:
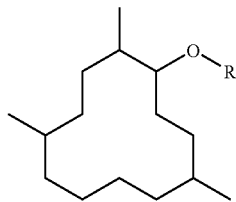 (7a')
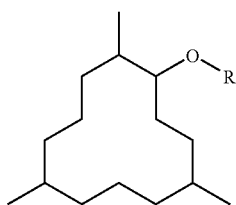 (7b')
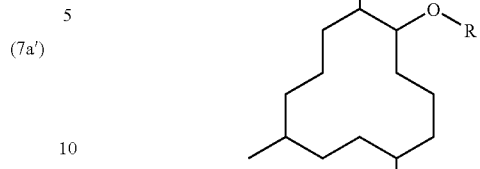 (7c')
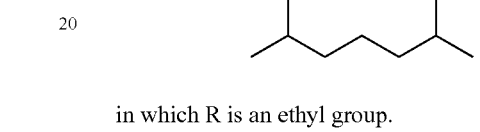 (7d')
in which R is an ethyl group.
* * * * *